(12) United States Patent
Kreuzer et al.

(10) Patent No.: US 9,918,890 B2
(45) Date of Patent: Mar. 20, 2018

(54) SURGICAL TABLE WITH MOVEABLE PERINEAL POST

(71) Applicant: Innovative Orthopedic Technologies, LLC, Houston, TX (US)

(72) Inventors: Stefan Kreuzer, Houston, TX (US); Joseph W. Pieczynski, II, Austin, TX (US)

(73) Assignee: Innovative Orthopedic Technologies, LLC, Houston, TX (US)

( * ) Notice: Subject to any disclaimer, the term of this patent is extended or adjusted under 35 U.S.C. 154(b) by 578 days.

(21) Appl. No.: 14/376,781

(22) PCT Filed: Feb. 6, 2013

(86) PCT No.: PCT/US2013/024962
§ 371 (c)(1),
(2) Date: Aug. 5, 2014

(87) PCT Pub. No.: WO2013/119688
PCT Pub. Date: Aug. 15, 2013

(65) Prior Publication Data
US 2015/0290064 A1     Oct. 15, 2015

Related U.S. Application Data

(60) Provisional application No. 61/595,444, filed on Feb. 6, 2012.

(51) Int. Cl.
*A61F 5/04* (2006.01)
*A61G 13/00* (2006.01)
(Continued)

(52) U.S. Cl.
CPC ............ *A61G 13/0036* (2013.01); *A61F 5/04* (2013.01); *A61F 5/3761* (2013.01);
(Continued)

(58) Field of Classification Search
CPC .................................................. A61G 13/0036
See application file for complete search history.

(56) References Cited

U.S. PATENT DOCUMENTS 2,691,979 A * 10/1954 Watson ..................... A61F 5/04
602/39
3,090,381 A * 5/1963 Watson .............. A61G 13/0036
5/624

(Continued)

OTHER PUBLICATIONS

Australian Examination Report dated Nov. 2, 2016, for Australian Application No. 2013217089 (6 p.).

(Continued)

*Primary Examiner* — Tarla Patel
(74) *Attorney, Agent, or Firm* — Conley Rose, P.C.

(57) ABSTRACT

A system for securing and manipulating a patient during a medical procedure comprises a support assembly coupled to a bed and configured to support a patient's leg. In addition the system comprises a rail coupled to the support assembly. The rail has a longitudinal axis, a first end, and a second end opposite the first end. In addition, the system comprises a perineal post movably mounted to the rail and oriented in a generally vertical direction. The post assembly is configured to move axially along the rail between a first position and a second position.

18 Claims, 10 Drawing Sheets

(51) Int. Cl.
*A61G 13/02* (2006.01)
*A61G 13/12* (2006.01)
*A61G 13/10* (2006.01)
*A61F 5/37* (2006.01)

(52) U.S. Cl.
CPC .......... *A61G 13/0081* (2016.11); *A61G 13/02* (2013.01); *A61G 13/101* (2013.01); *A61G 13/12* (2013.01); *A61G 13/123* (2013.01); *A61G 13/1245* (2013.01); *A61G 13/1265* (2013.01); *A61G 2210/50* (2013.01)

(56) References Cited

U.S. PATENT DOCUMENTS

| | | | | |
|---|---|---|---|---|
| 6,385,802 | B1* | 5/2002 | Roberts | A61G 13/0009 5/612 |
| 7,832,401 | B2* | 11/2010 | Torrie | A61G 13/0036 128/845 |
| 8,997,286 | B2* | 4/2015 | Wyslucha | A61G 13/0036 378/209 |
| 2002/0023298 | A1* | 2/2002 | Lamb | A61G 13/0036 5/600 |
| 2004/0133979 | A1* | 7/2004 | Newkirk | A61G 13/0036 5/600 |
| 2006/0185090 | A1* | 8/2006 | Jackson | A61G 7/001 5/621 |
| 2007/0265635 | A1* | 11/2007 | Torrie | A61G 13/0036 606/105 |
| 2010/0154121 | A1 | 6/2010 | Swain, Jr. | |
| 2011/0023893 | A1* | 2/2011 | Striggow | A61G 13/12 128/882 |
| 2011/0190676 | A1 | 8/2011 | Torrie et al. | |

OTHER PUBLICATIONS

PCT/US2013/024962 International Search Report and Written Opinion dated May 13, 2013 (11 p.).

* cited by examiner

US 9,918,890 B2

SURGICAL TABLE WITH MOVEABLE PERINEAL POST

CROSS-REFERENCE TO RELATED APPLICATIONS

This application is a 35 U.S.C. § 371 national stage application of PCT/US2013/024962 filed Feb. 6, 2013 and entitled "Surgical Table with Moveable Perineal Post," which claims priority to U.S. Provisional Application No. 61/595,444 filed Feb. 6, 2012 and entitled "Surgical Table with Moveable Perineal Post," both of which are hereby incorporated herein by reference in their entirety for all purposes.

STATEMENT REGARDING FEDERALLY SPONSORED RESEARCH OR DEVELOPMENT

Not applicable.

BACKGROUND

This disclosure relates generally devices and methods for diagnostic analysis and performing surgeries. More particularly, this disclosure relates to devices and methods for supporting and manipulating a patient's leg during surgery (e.g., hip joint surgery) and for diagnostic analysis of the leg (e.g. x-ray).

During diagnostic evaluation of a patient's leg or surgery on a patient's leg (e.g., hip or knee surgery), certain positions and orientations of the leg and/or hip joint may be preferred. For example, during one phase of hip surgery, the surgeon may want to place the patient's leg in tension (i.e., traction) at an angle with respect to the spine or the pelvis, whereas in another phase of hip surgery, the surgeon may want to change the angle of the patient's leg or rotate the patient's leg. In some cases, the surgeon may want to maintain traction or a particular rotational orientation of the patient's leg while adjusting the position of the leg or the patient's position on the surgical table.

Conventional surgical tables designed for use in leg surgeries typically include a vertically oriented perineal post that is fixed to the table, and positioned between the patient's legs against the perineum during surgery. The perineal post functions to maintain the patient's position on the surgical table while a patient's leg is pulled inferiorly (i.e., generally away from the patient's torso). This enables the application of inferior traction to the patient's leg by applying tension generally along the length of the leg. However, for some surgeries and diagnostic evaluations, it may be desirable to apply lateral traction to the femur to distract the hip joint laterally. Although conventional surgical tables and associated traction devices enable the application of inferior traction, they typically do not provide an ability to controllably apply lateral traction to the femur.

BRIEF SUMMARY OF THE DISCLOSURE

These and other needs in the art are addressed in one embodiment by a surgical system for positioning a patient's leg during a medical procedure. In an embodiment, the system comprises a support assembly coupled to a bed and configured to support a patient's leg. In addition, the system comprises a vertically oriented perineal post moveably coupled to the bed. The perineal post is configured to move laterally relative to the bed.

These and other needs in the art are addressed in another embodiment by an operating table system. In an embodiment, the system comprises a support assembly configured to retain each of a patient's legs and reversibly coupled to a bed. In addition, the system comprises a bolster coupled to the bed adjacent to a support assembly. Further, the system comprises a rail coupled to the bed, the rail having a longitudinal axis, a first end, and a second end opposite the first end. Still further, the system comprises a vertical perineal post movably mounted to the rail. The post assembly is configured to move axially along the rail between a first position and a second position.

These and other needs in the art are addressed in another embodiment by a method for applying traction to a patient. In an embodiment, the method comprises securing a patient's feet to a support member to support the patient's legs distal from a bed. In addition, the method comprises a positioning a perineal post between the patient's legs. Further, the method comprises laterally repositioning the perineal post to apply lateral traction to the patient's leg.

Embodiments described herein comprise a combination of features and advantages intended to address various shortcomings associated with certain prior devices, systems, and methods. The foregoing has outlined rather broadly the features and technical advantages of the invention in order that the detailed description of the invention that follows may be better understood. The various characteristics described above, as well as other features, will be readily apparent to those skilled in the art upon reading the following detailed description, and by referring to the accompanying drawings. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
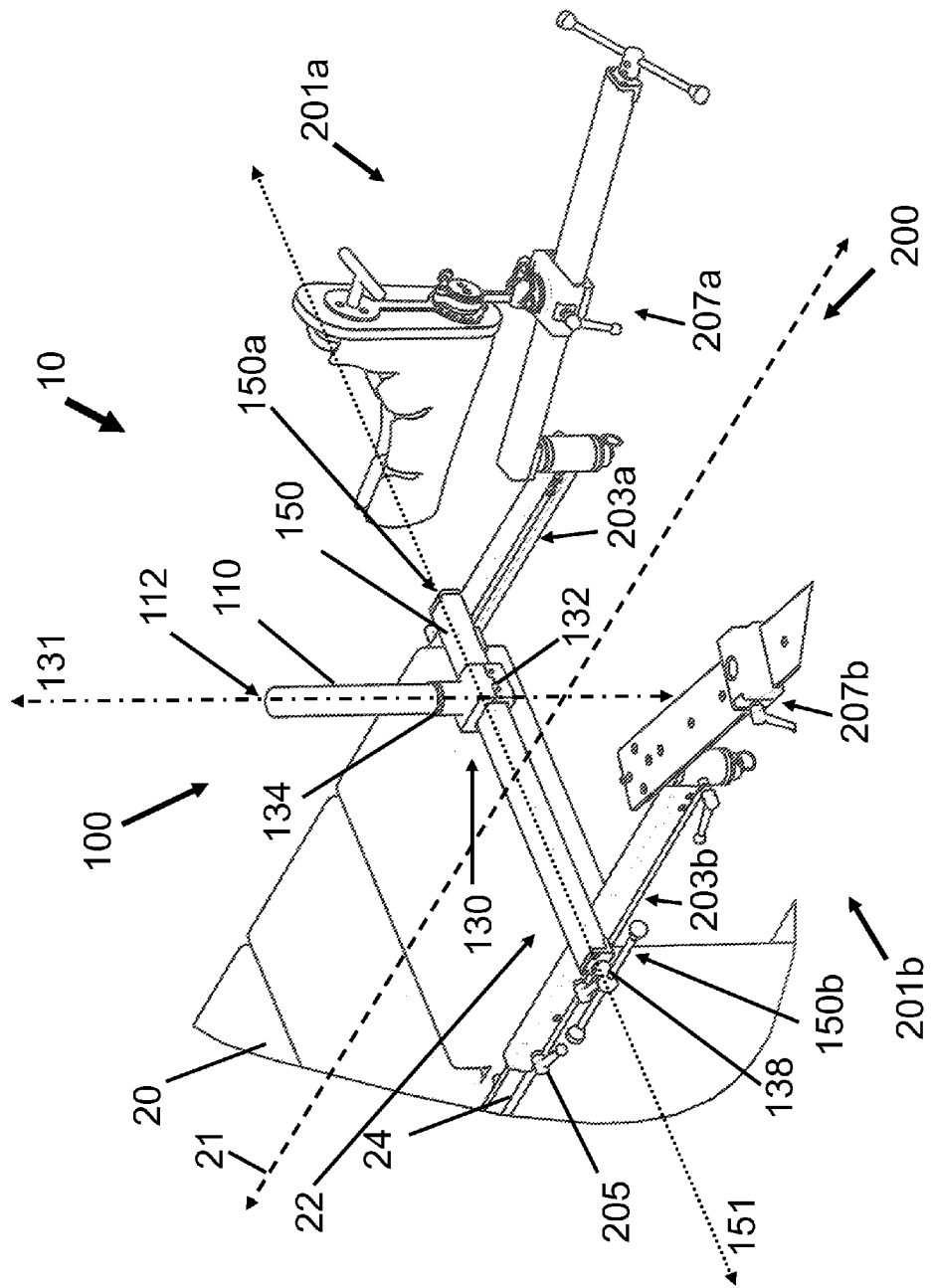
FIG. 1 is a perspective view of an embodiment of a system in accordance with the principles described herein for applying inferior and/or lateral traction to a patient's femur.
Figure 2:
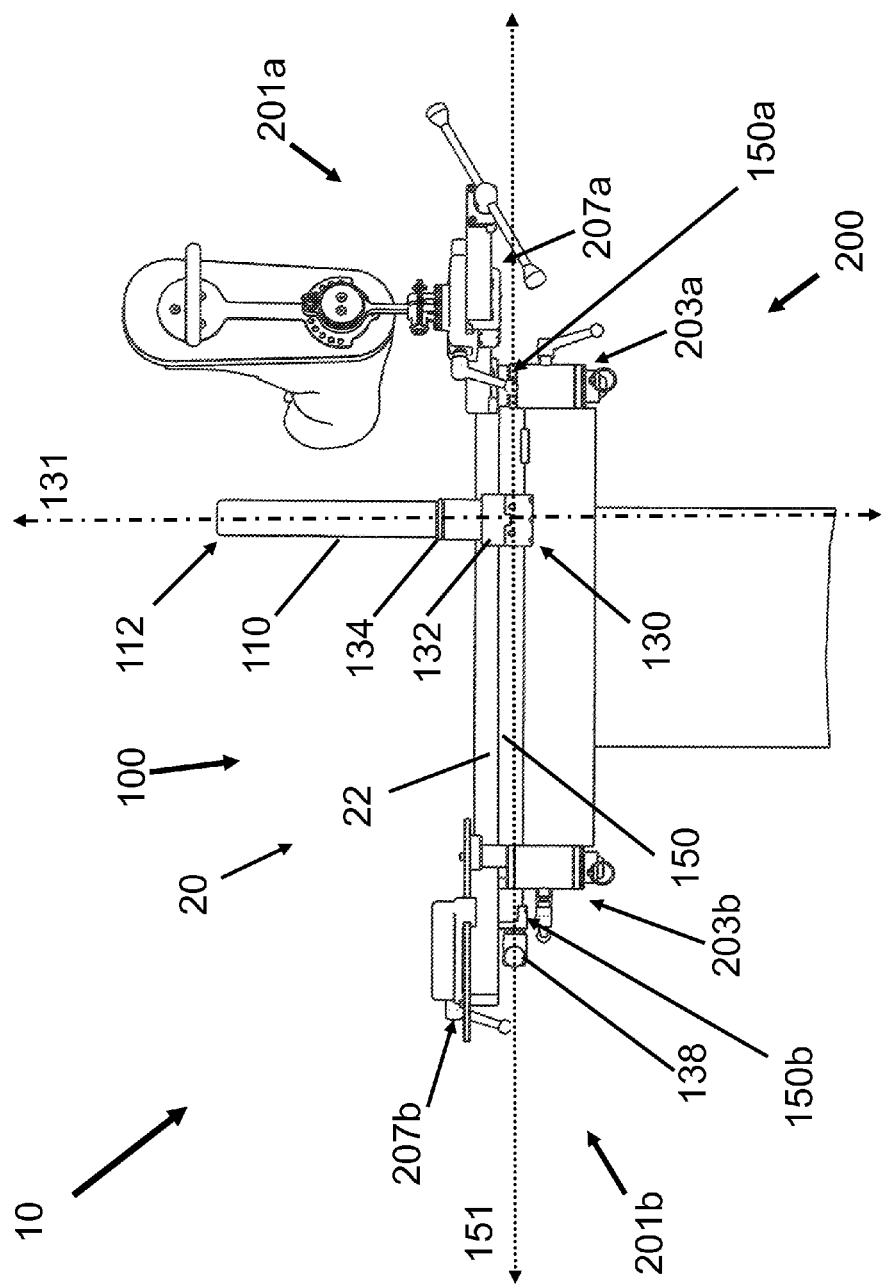
FIG. 2 is an end view of the post assembly of FIG. 1.
Figure 3:
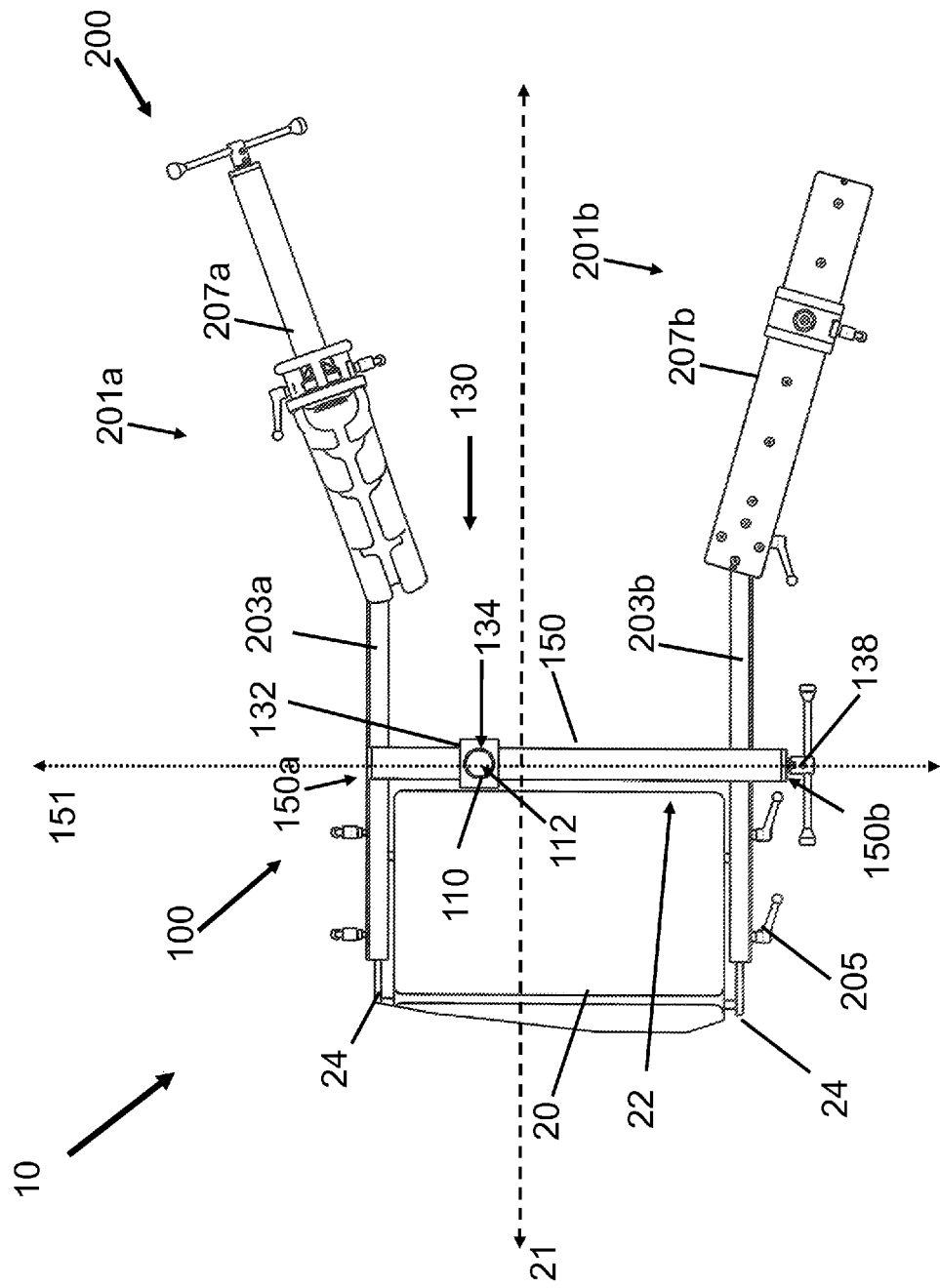
FIG. 3 is a top view of the post assembly of FIG. 1.
Figure 4:
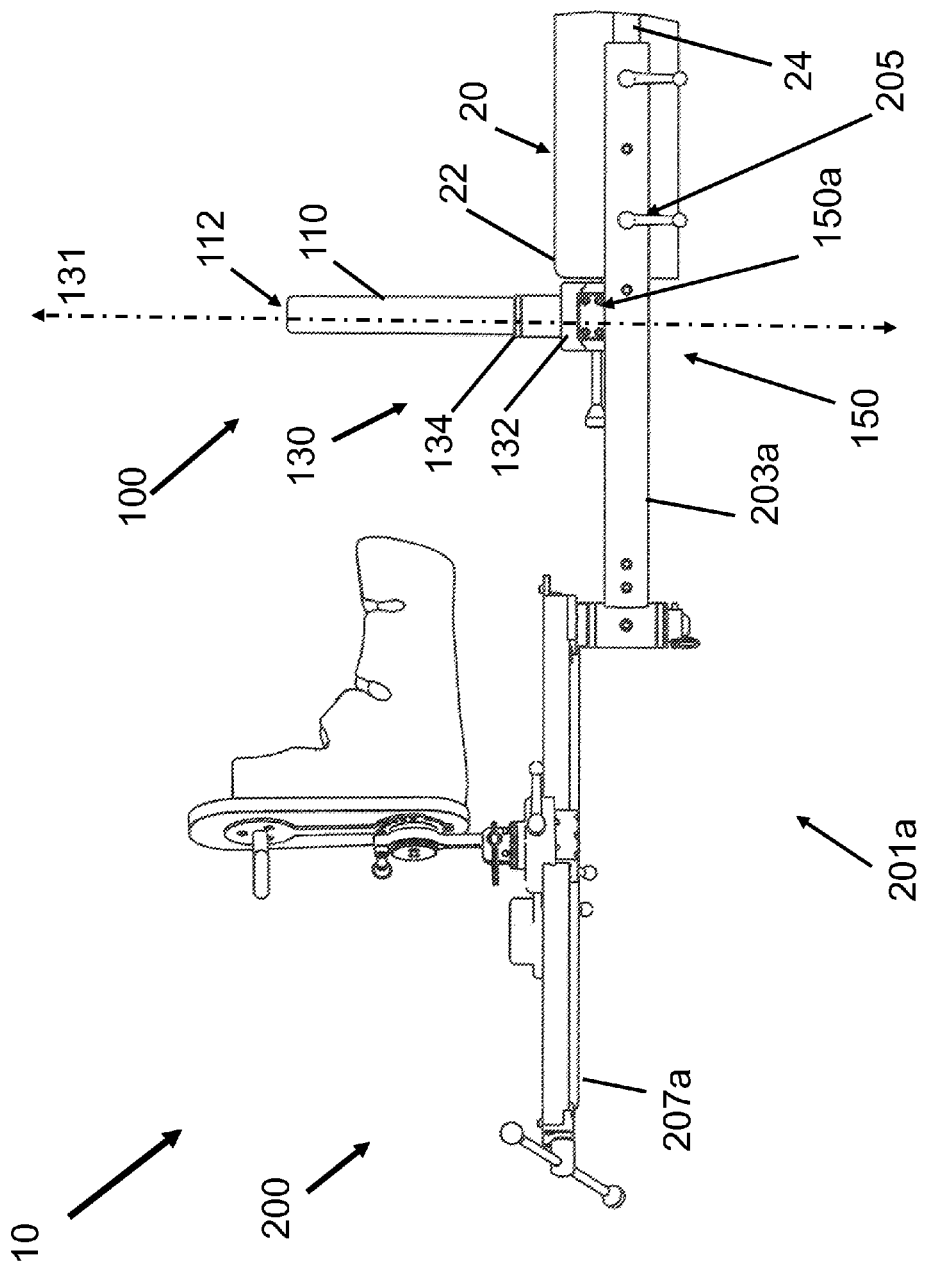
FIG. 4 is a side view of the post assembly of FIG. 1.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis. Additionally, as used herein, the terms "bed" and "table" refer to a patient bed, operating table, an examination bed, or other medical bed or table used for medical procedures, operations, diagnostics, and care.

Referring now to FIG. 1, an embodiment of a system 10 for adjustably restraining a patient's body and lower limb (i.e., leg) during surgery or diagnostic evaluation is shown. In this embodiment, system 10 comprises a modular post assembly 100 disposed at an end 22 of an operating table or bed 20 and a lower limb support system 200 extending from post assembly 100 and bed 20. The post assembly 100 includes a perineal post 110, a rail 150, and a mount 130 moveably coupling post 110 to rail 150. An actuation device or control 138 is provided to position and move post 110 along rail 150. In this embodiment, rail 150 is removably coupled to limb support system 200, which in turn is removably coupled to bed 20. Rail 150 preferably comprises a material that is at least partially X-ray transparent (e.g., carbon fiber) to allow X-rays to pass therethrough in route to an X-ray cassette generally disposed below rail 150. Post 110 is positioned between the patient's legs, in contact with the perineum to permit the application of traction to the patient's leg(s). Post assembly 100 and support system 200 are used together to manipulate a patient's legs and feet, and apply traction (inferior and/or lateral traction) to facilitate a procedure or examination.

Generally, all components of system 10 are constructed of a material that may be sterilized, for example by an autoclave. Suitable materials include, without limitation, composites, plastics, metals and metal alloys (e.g., stainless steel), or combinations thereof. Additionally, system 10 is modular, such that any of the components of system 10 can be disconnected and replaced without having to replace the entirety of system 10.

As previously described, system 10 is configured such that it may be completely sterilized. However, referring now to FIG. 1, since system 10 is modular, it may be differentially sterilized (e.g., only select components of system 10 may be sterilized) dependent on a surgeons preferences and/or the procedure being performed. For instance, as is known in the art, sterile drapes are used to cover and isolate unsterilized equipment in an operating room from the patient, surgeon, other medical personnel, or combinations thereof. Components positioned below the drape are not necessarily sterilized while those components positioned above the drape and exposed are sterilized to reduce the potential for infections. Accordingly, in embodiments described herein, a sterile drape can be positioned such that the entirety of the system 10 (including the support system 200, rail 150, and post 110) are exposed, and hence, sterilized. Alternatively, the sterile drape can be positioned to isolate select components of system 10 such that certain components are exposed and sterilized, whereas other components are covered and isolated, and hence, may not necessarily be sterilized. For example, support system 200 can be covered by a drape with rail 150 and post 110 exposed, or with only post 110 exposed (e.g., passes upward through a hole in the sterile drape). As another example, for ease of access and operation during a procedure, control 138 preferably extends beyond sterile drape (i.e. control 138 is preferably exposed and sterilized).

In embodiments described herein, bed 20 generally supports the patient's torso and pelvis, while support system 200 supports the patient's legs. In general, support system 200 may comprise any apparatus or any assembly that is configured to support and manipulate a patient's legs. Examples of suitable leg support systems that may be used in place of system 200 are disclosed in U.S. patent application Ser. No. 13/418,169, which is hereby incorporated herein by reference in its entirety.

Referring now to FIGS. 1 to 7, support system 200 is configured to support the legs of the patient as they extend from the end 22 of bed 20. In this embodiment, support system 200 includes a left support assembly 201a and a right support assembly 201b that independently support and manipulate the patient's corresponding legs and feet. In other embodiments, the support system (e.g., system 200) may include only a left support assembly 201a or a right support assembly 201b. In addition, in this embodiment, left assembly 201a and right assembly 201b are interchangeable or reversible such that each can be positioned for use and used for either leg (i.e., the right leg or the left leg). Assemblies 201a, 201b are coupled to bed 20 with a first support portion 203a, 203b, respectively. Each first support portion 203a, 203b slidably engages a corresponding side rail 24 of bed 20 and extends parallel to a longitudinal axis 21 of bed 20. Further, each first support portion 203a, 203b comprises at least one quick release connector 205 to releasably lock onto a corresponding bed rail 24. In this embodiment, each quick release connectors 205 comprises an externally threaded shaft having an outer end attached to a handle and an inner end that bears against rail 24. The shaft extends through a mating internally threaded hole in the corresponding support portion 203a, 203b, and thus, by rotating the shaft with the handle, the shaft is moved into and out of engagement with the corresponding rail 24.

Referring still to FIGS. 1 to 7, rail 150 has a central or longitudinal axis 151, a first end 150a, and a second end 150b opposite end 150a. Mount assembly 130 is slidably disposed about rail 150, and post 110 extends upward from mount assembly 130. Rail 150 supports mount assembly 130 and post 110. In this embodiment, axis 151 is an elongate, linear member, however, in general, rail 150 and axis 151 can have other suitable shapes, such as curved. In addition, in this embodiment, rail 150 has a rectangular C-shaped cross-sectional shape, however, in general, rail 150 can have other suitable cross-sectionals shapes such as rectangular, circular, polyhedral, or quadrilateral. The outer surface of rail 150 is smooth to facilitate smooth and even movement of mount assembly 130 along rail 150.

Rail 150 is oriented perpendicular to axis 21 in top view and extends between first support portions 203a, 203b. In particular, end 150a of rail 150 is coupled to first support portion 203a and end 150b of rail 150 is coupled to first support portion 203b. In particular, ends 150a, 150b are releasably and reversibly mounted to support portions 203a, 203b. For example, ends 150a, 150b may be bolted to or screwed to support portions 203a, 203b. Alternatively, a quick release connector (not shown) such as quick release connector 205 can be positioned at each end 150a, 150b to releasably couple rail 150 to support portions 203a, 203b. In still other embodiments, ends 150a, 150b of rail 150 are moveably coupled to support portions 203a, 203b such that ends 150a, 150b can be moved back-and-forth along support portions 203a, 203b and positioned in any desired position thereon.

Although rail 150 is directly attached to support portions 203a, 203b in this embodiment, in other embodiments, the rail (e.g., rail 150) can be configured to attach directly to the bed (e.g., bed 20, the end 22 of bed 20, or rails 24). However, in such alternative embodiments, the rail is preferably positioned so as not to interfere with any leg supports (e.g., support portions 203a, 203b) that are present, if any.

Referring still to FIGS. 1 to 7, mount assembly 130 is slidably mounted to rail 150, and vertical post 110 is fixably secured to mount assembly 130. Thus, post 110 does not move rotational or translationally relative to mount assembly 130, however, mount assembly 130 and post 110 can move together axially (relative to axis 151) back and forth along rail 150 between ends 150a, 150b. In this embodiment, mount assembly 130 includes a body 132 disposed about rail 150 and having a post interface 134. To prevent body 132 from inadvertently disengaging rail 150, body 132 preferably encircles at least 75% of the perimeter of rail 150. In this embodiment, body 132 extends completely around rail 150. Post interface 134 is disposed above rail 150 and retains post 110 in a vertical orientation. In particular, post 110 has a vertical central or longitudinal axis 131 oriented orthogonal to horizontal axes 21, 151.

In general, post interface 134 can comprise any means for coupling post 110 to body 132. Post interface 134 preferably comprises a resilient, reversible, or pivotable interface such that post 110 and axis 131 is at least partially re-positionable with respect to the axis 151. For example, post interface 134 may comprise a threaded engagement, a twist-lock engagement, or an interference engagement. In instances, the post interface 134 may comprise a bearing in order to rotate post 110 about axis 131 to facilitate manipulation during a procedure without irritating the patient. In certain instances, post interface 134 comprises a semi-rigid, resilient coupling that allows post 110 to resist traction forces, but does flex and bend relative to body 132 to a limited extent to minimize bruising of the patient. In further configurations, the post interface 134 is a ball and socket or similar device that is configurable to permit post 110 to pivot or swivel relative to the body. Without limitation, post interface 134 may be configured to permit post 110 to achieve a position that is parallel to rail 150 or bed 20.

Figure 5:
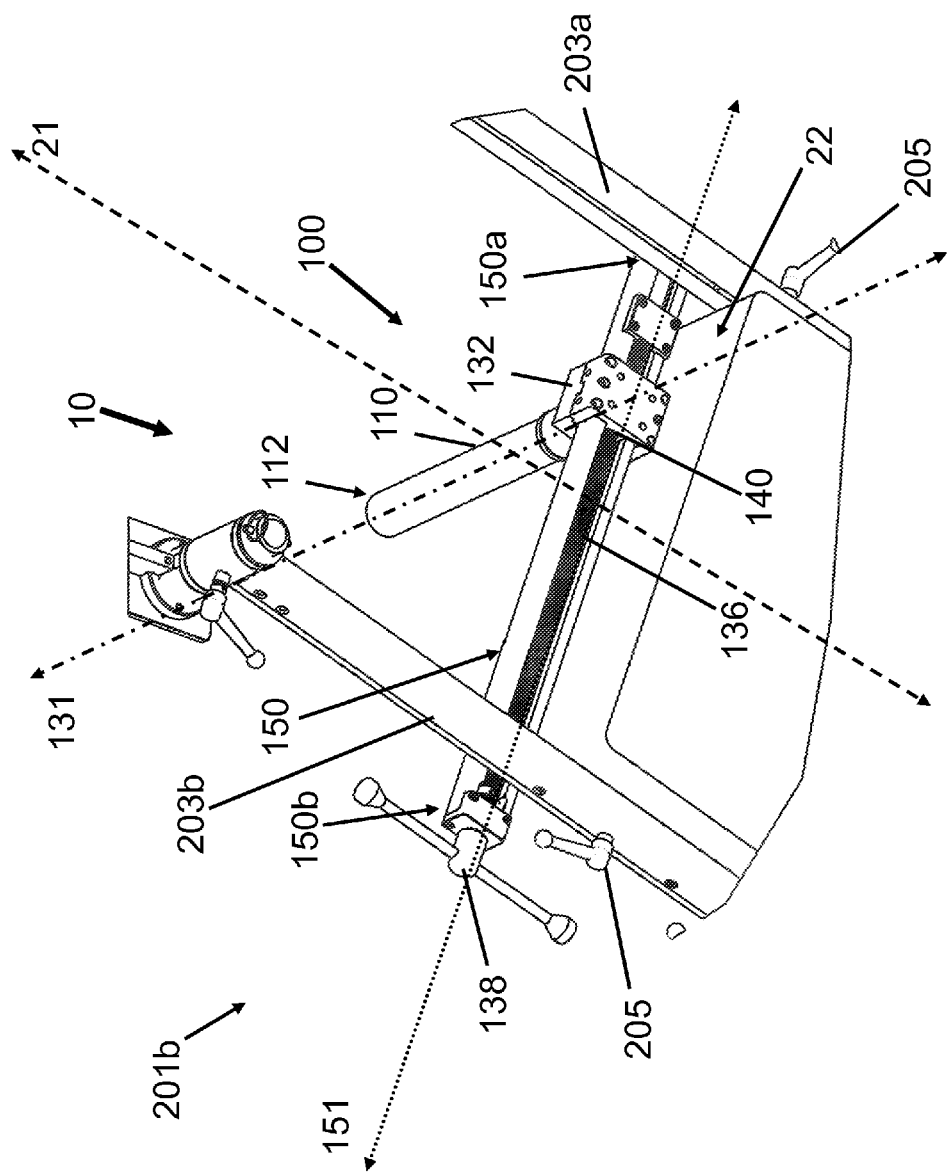
FIG. 5 is a perspective bottom view of the post assembly of FIG. 1.
Figure 6:
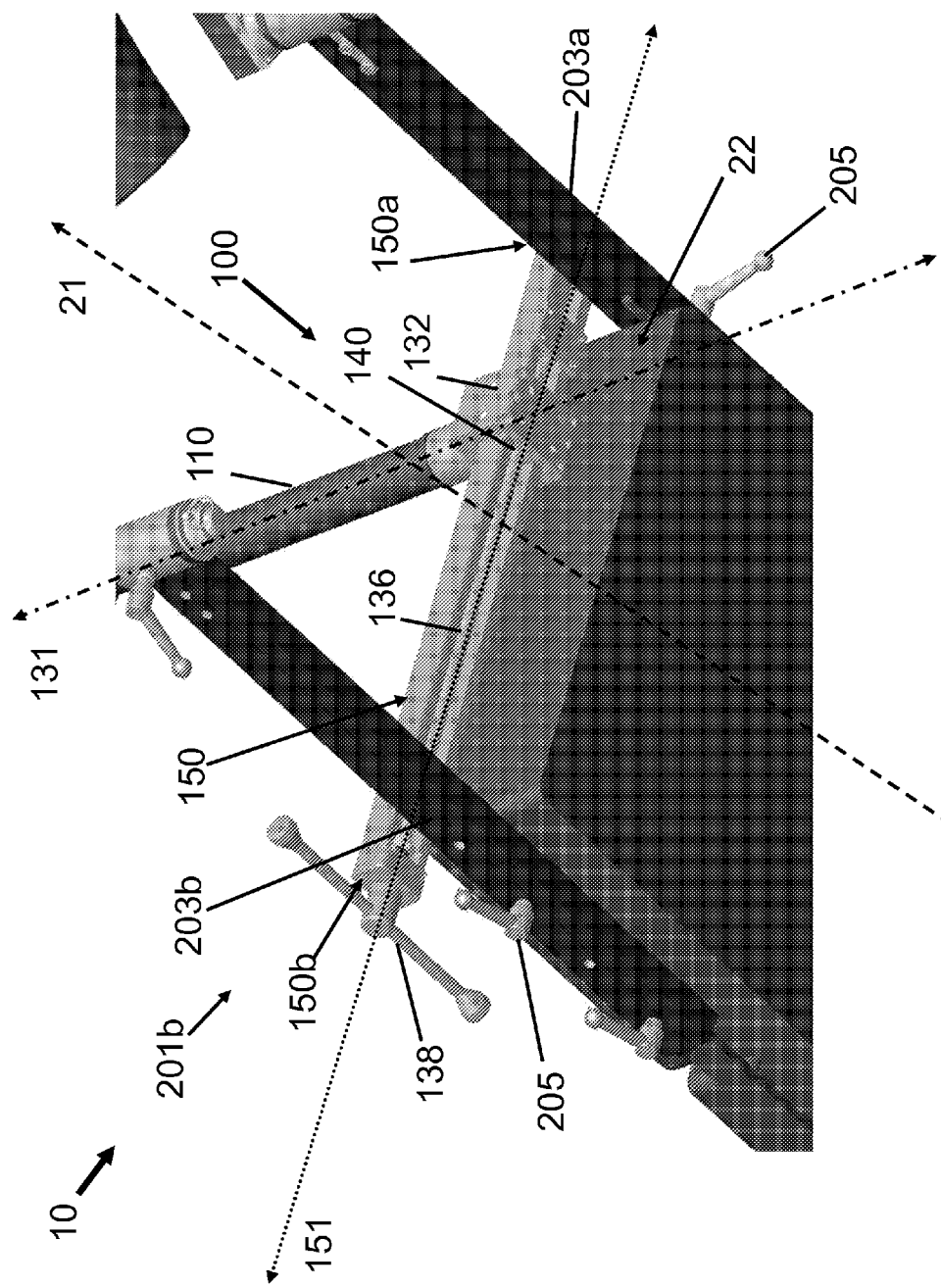
FIG. 6 is a perspective bottom view of the post assembly of FIG. 1.
Figure 7:
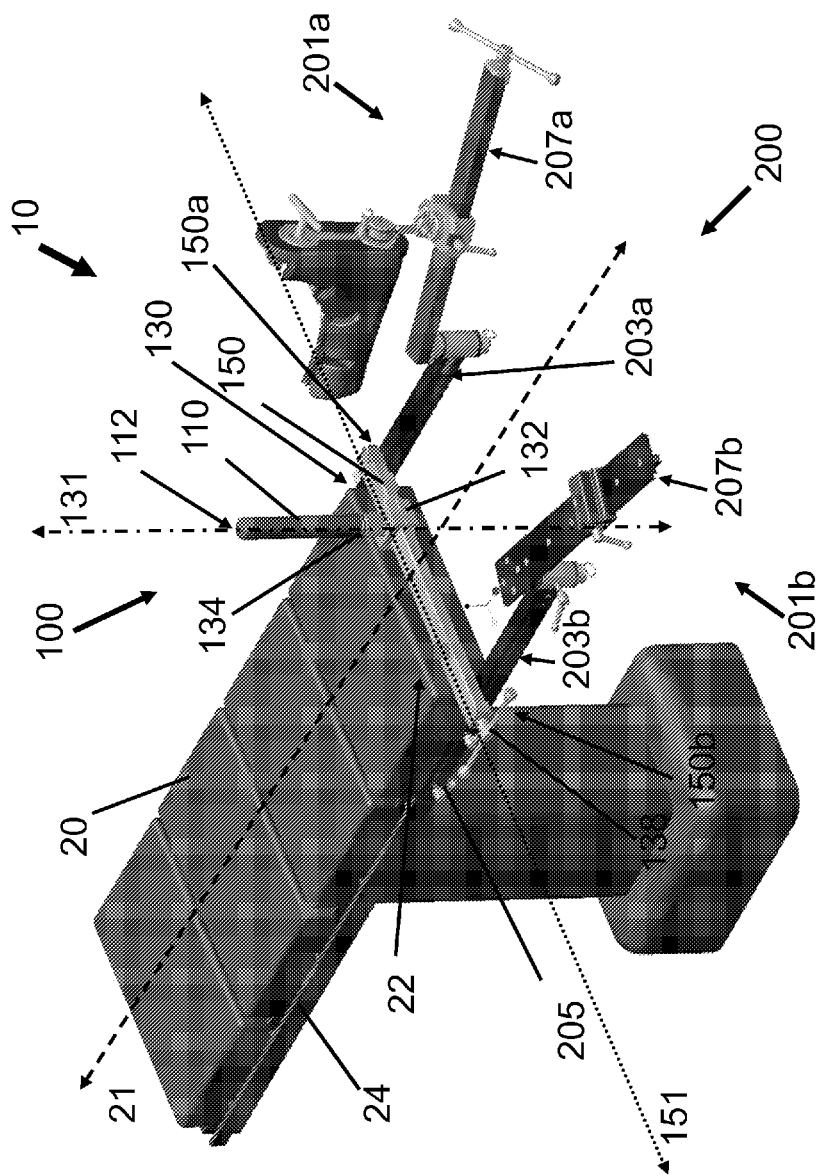
FIG. 7 is a perspective view of the system of FIG. 1.

Referring now to FIGS. 1, 5 and 6, assembly 130 is moveably coupled to rail 150. More specifically, body 132 is coupled to an actuator 136 disposed in a channel extending axially along the bottom of rail 150. In this embodiment, actuator 136 is a threaded shaft that threadably engages an internally threaded aperture 140 in body 132, thereby enabling mount assembly 130, and hence post 110, to be moved axially between ends 150a, 150b by rotating actuator 136 with controller 138. In this embodiment, controller 138 is a handle coupled to end 150b of rail 150. In general, controller 138 can be positioned proximal the patient's operative leg or the non-operative leg (e.g., left or right leg). The direction of movement of rail assembly 130 depends on the direction of rotation of actuator 136. For example, when actuator 136 is rotated in a first direction with controller 138, mount assembly 130 moves axially along rail 150 in a first direction, and when actuator 136 is rotated in the opposite direction with handle 138, mount assembly 130 moves axially along rail 150 in the opposite direction.

Although axial movement of assembly 130 is manually controlled via engagement of a threaded shaft and threaded aperture in this embodiment, in general, the axial movement of the mount assembly (e.g., mount assembly 130) can be accomplished manually or automatically. For example, a linear actuator such as an electric, a hydraulic or a pneumatic actuator can be coupled to mount assembly 130 to move it along rail 150, or a motor can be coupled to the threaded shaft to drive the rotation of the threaded shaft in either direction to move mount assembly 130 along rail. In such embodiments, the controller for the actuator or motor can be positioned remotely from the rail 150 or on any portion of the bed 20, and can be operated through a wired or wireless connection. For example, the controller can be a foot pedal that allows the surgeon to control the movement of mount assembly along rail 150 without the use of his/her hands. Also, in embodiments utilizing manual control of the position and movement of the mount assembly, quick release locks may be employed to lock the mount assembly in place at the desired axial position.

Referring again to FIGS. 1 to 7, post 110 is configured for positioning between a patient's legs or perineum. Post 110 preferably has an axial length between about 30 cm and about 50 cm measured along axis 131 from body 132. Further, the outer surface of the upper end 112 of post 110 is rounded and smooth to prevent the snagging of medical equipment, wires, air-hoses, and clothing.

Post 110 is configured to resist traction forces applied to the patient's leg(s) and retain the patient's position on bed 20. For example, the post 110 may be configured rotate about the axis 131 to facilitate patient manipulation during a procedure. Post 110 is preferably covered with padding or other means to distribute forces applied to the patient's body during a procedure. Alternatively, the post (e.g., post 110) can be configured to deflect incrementally in response to forces applied to the patient's body during a procedure. In further embodiments, the post 110 can be configured to pivot relative to body 132 for example by a ball and socket or similar pivotable joint positioned in the post interface 134. In embodiments, the post 110 may be pivoted to achieve a configuration that is parallel with the rail 150 or the bed 20.

Figure 8:
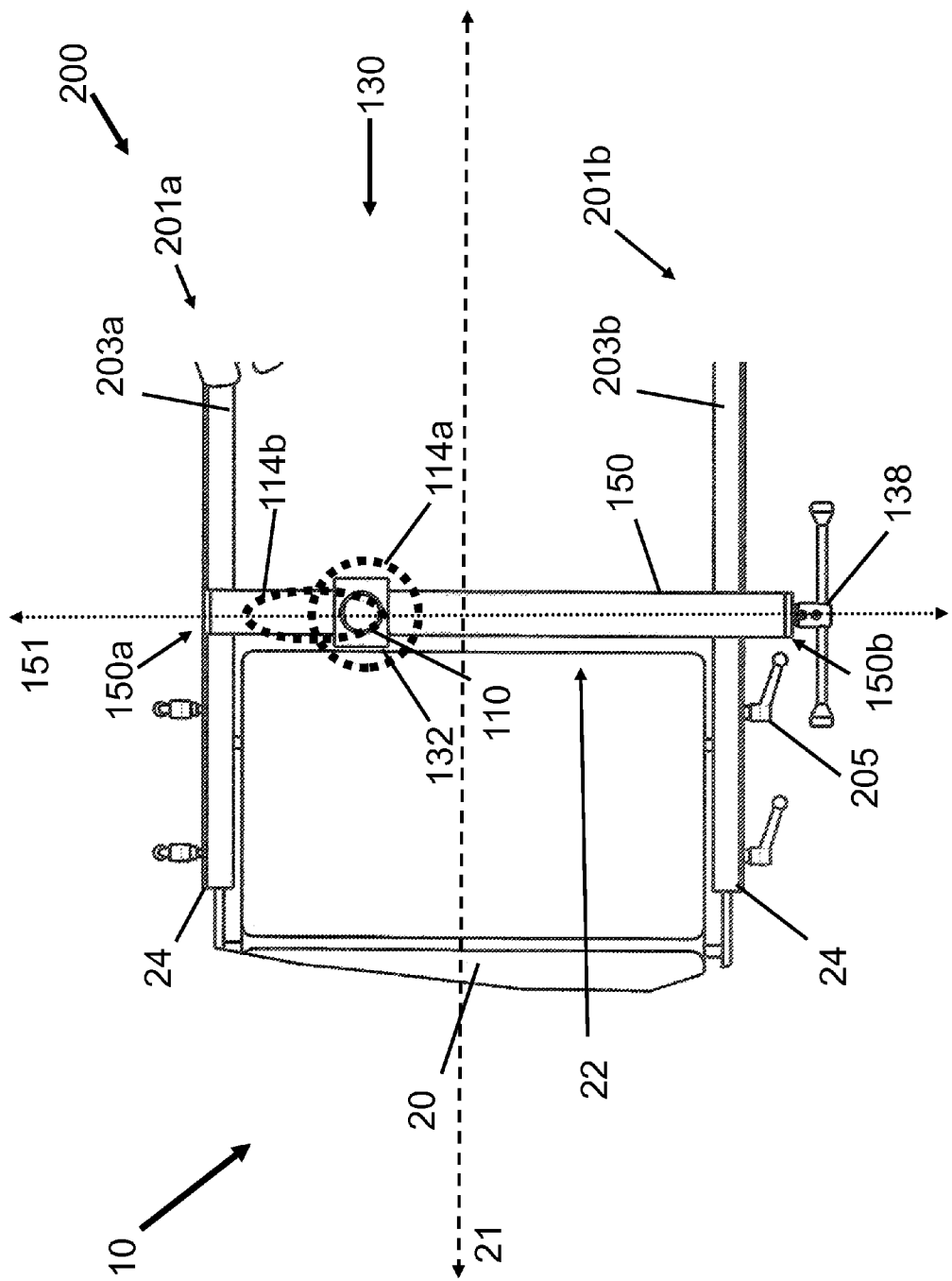
FIG. 8 is a top view of an embodiment of a post assembly in accordance with the principles described herein for applying inferior and/or lateral traction to a patient's femur.

Referring now to FIG. 8, post 110 can include at least one expandable inner chamber 114 formed by a bladder, jacket, cover, ring, or pocket that can be pressurized and depressurized by a fluid (i.e. air or liquid) to expand and contract, respectively. The material defining chamber 114 is a flexible, resilient material capable of expanding and contracting in response to an increase or decrease, respectively, in internal pressure or a fluid volume. In this embodiment, chamber 114 extends the length of post 110, however, in general, the chamber (e.g., chamber 114) can extend any desired length along post 110. The chamber 114 is differentially controlled to permit incremental or partial expansion and deflation. In some instances, differential expansion of chamber 114 comprises inflation of a portion of chamber 144 or one of a plurality of sub-chambers. Further, the chamber 114 is configured to expand radially from post 110, for example to a first expanded position 114A. Alternatively, the chamber 114 is configured to expand primarily in at least one direction, for example to a 2nd extended position 114B. Further, as illustrated chamber 114B may be configured to have differential elasticity in order to control the direction of the inflation. For example, the chamber 114B is more elastically deformable perpendicular to axis 21 and parallel to axis 151, such that chamber 114B expands laterally thereby applying lateral traction to a patient's leg.

Figure 9:
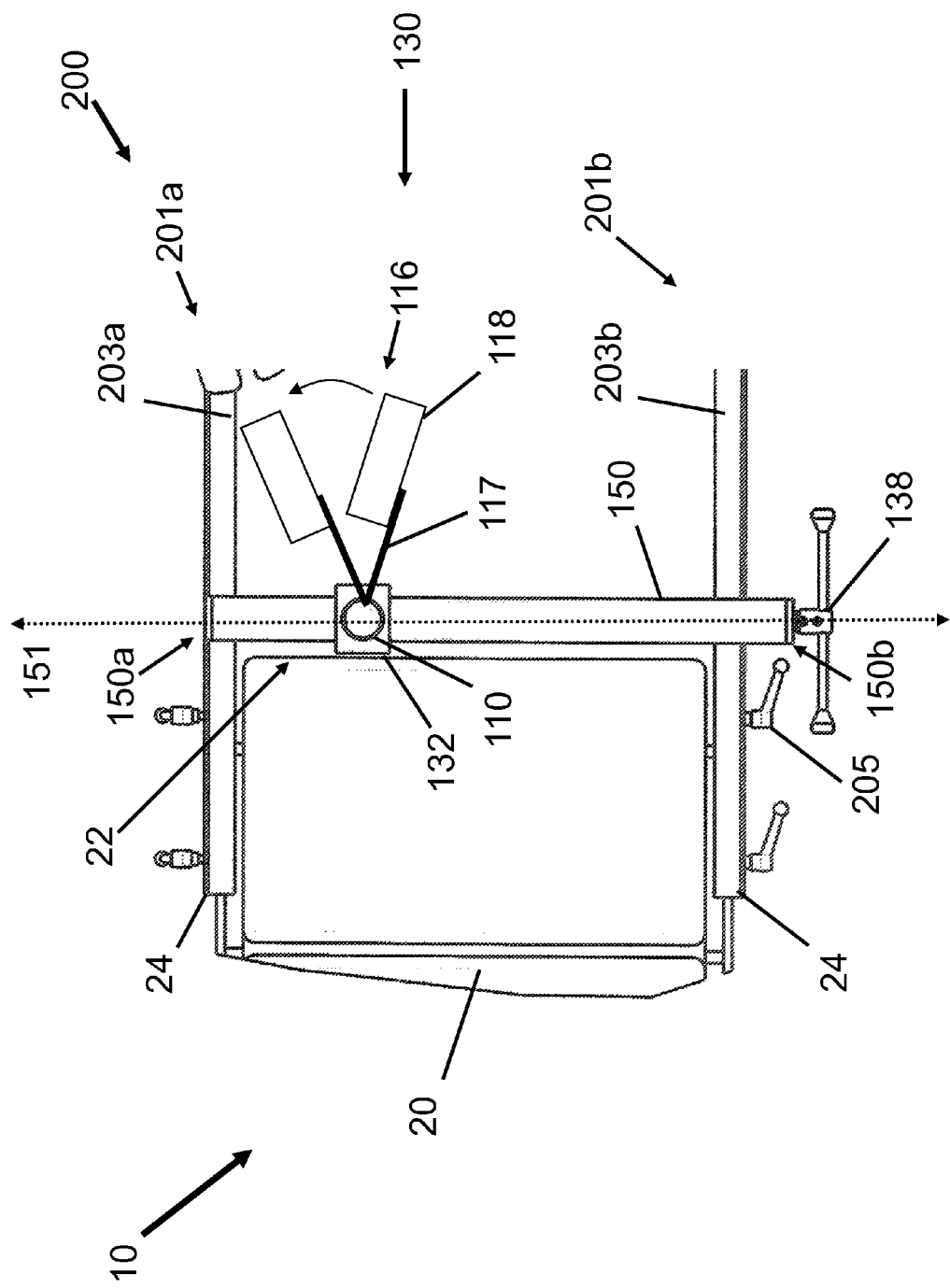
FIG. 9 is a top view of an embodiment of a post assembly in accordance with the principles described herein for applying inferior and/or lateral traction to a patient's femur.

Referring now to FIG. 9, in this embodiment, post 110 is provided with a pad assembly 116 having at least one arm 117 and pad 118. Pad assembly 116 is configured to rotate about axis 131 in any direction to reposition and retain a patient's leg in desired position. Pad 118 comprises any cushion or other interface configured to contact patient's leg. Pad 118 may comprise a pocket, pouch, or chamber that can be pressurized and expanded to provide additional support or motivation to patient's leg.

Figure 10:
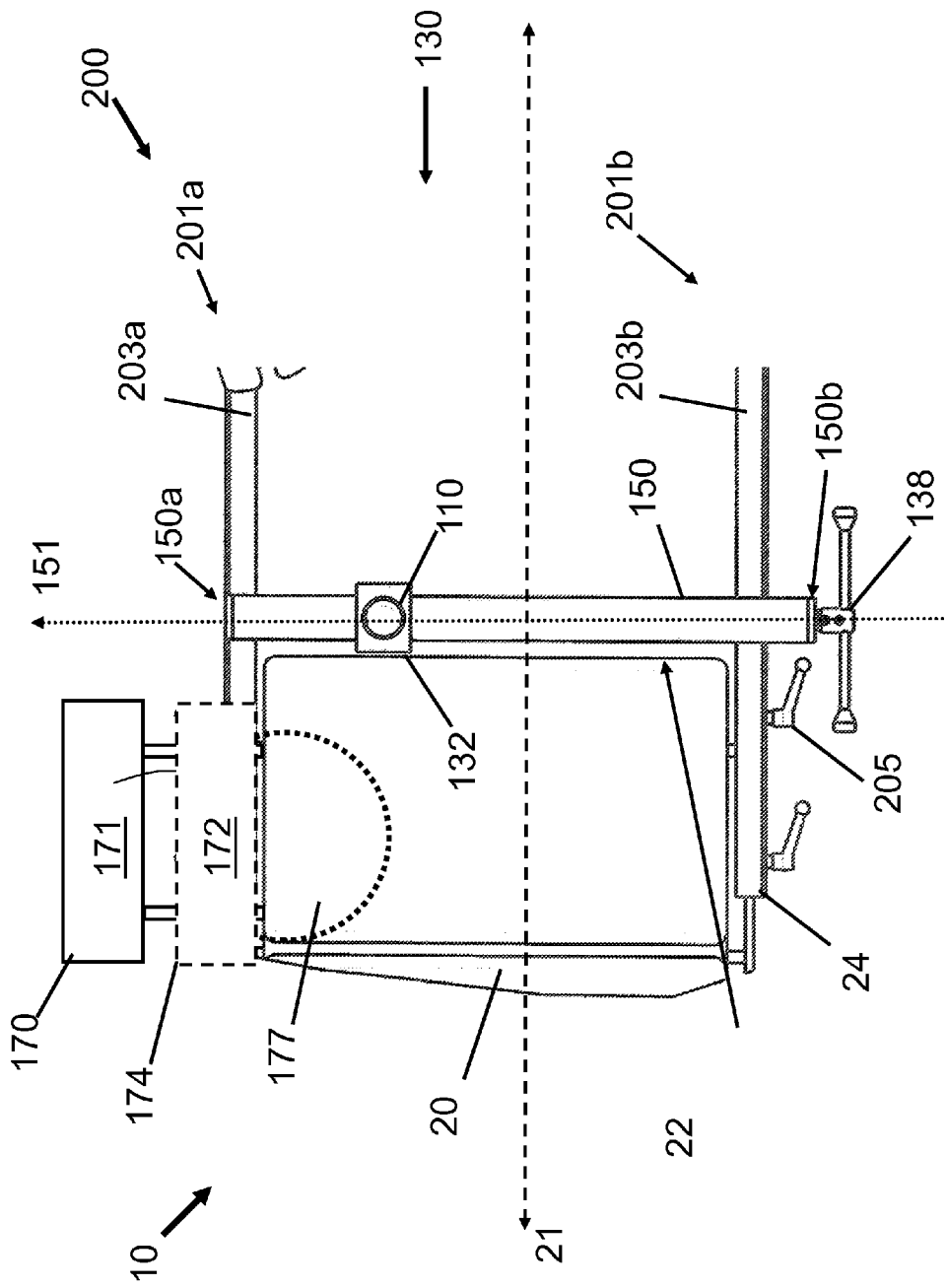
FIG. 10 is a top view of an embodiment of a cushion in accordance with the principles described herein for applying inferior and/or lateral traction to a patient's femur.

Referring now to FIG. 10, a bolster 170 may be included in system 10 to contact, restrain, and support the patient's torso when lateral traction is applied with post 110. In this embodiment, bolster 170 comprises a cushion or pad configured to moveably attach to the bed 20 or rail 24. Bolster 170 is coupled to the bed 20 with a bolster support 174. In general, support 174 may comprise any connection allowing lateral movement of bolster 170. Thus, bolster 170 is configured to move laterally with respect to axis 21 chamber between a first position 171 and a second position 172. Bolster 170 includes a control that is the same as control 138 previously described for moving bolster 170 laterally between positions 171, 172.

In this embodiment, bolster 170 also includes an inner chamber 177 configured to expand in response to an increase in internal pressure, for example fluid pressure (i.e. gas or liquid). The material of bolster 170 defining chamber 177 is constructed of a flexible, resilient material capable of expanding and contracting in response to an increase in internal pressure. The pressure within chamber 177 is controlled to permit incremental or partial expansion and deflation.

As described above, system 10 is employed for medical and surgical procedures related to the assessment and treatment of a patient's leg, pelvis, or both. During a procedure, the patient is secured to bed 20 with each leg secured to and supported by the respective support assembles 201a, 201b.

Rail 150 is coupled to the respective support assemblies 201a, 201b at a position adjacent the bed end 22. Further, the mount assembly 132 is positioned via control 138, such that post 110 extends between the patient's legs. Control 138 may extend beyond the sterile field proximal to the patient's operative leg, such that it is easily accessible by the surgeon. For instance, a sterilized modular control 138 may extend through a sterile drape that covers the remainder of system 10 such that the surgeon proximal the patient's hip joint can apply lateral traction using control 138.

During the procedure, lateral traction is applied to the patient's femur, pelvis, or both by (a) placing the corresponding leg in sufficient traction with the corresponding leg support assembly 201a, b to restrict the patent from moving laterally; and (b) post 110 is expanded and/or moved laterally against the inside of the patient's upper leg. To reduce the likelihood of inadvertently moving the patient laterally or tilting the patient during application of lateral traction with post 110, prior to expanding and/or moving post 110 laterally, bolster 170 is preferably brought into engagement with the outside of the patient's torso or pelvis on the side to which post 110 will be moved laterally, and further, both of the patient's legs are preferably secured to the corresponding leg support assemblies 201a, b. The chamber 114 disposed on post 110 or the chamber 177 disposed on bolster 170 may be at least partially inflated or expanded to provide or supplement lateral traction applied to a patient's femur or pelvis to facilitate access to an internal structure. Further, chamber 114 and chamber 177 may be operated independent from the post 110 and the bolster 170 to provide traction or fine control of traction.

In the manner described, embodiments disclosed herein may be used to apply lateral traction to a patient's femur to distract the hip joint laterally during a procedure. This may be applied for enhanced access to the corresponding hip joint during surgery or for enhanced visualization of the corresponding hip joint during surgery or imaging. Application of lateral traction offers the potential to reduce reliance on purely axial traction, which can lead to palsy of the sciatic and femoral nerves if applied excessively and/or for an extended period of time.

While the forgoing provides an exemplary series of steps for a medical procedure a physician may operate system 10 in a different sequence. As such the terms primary adjustments and secondary adjustments should not be interpreted as preferred or sequential in meaning Additionally, the securing or constraining of rotation about all axes of rotation in the system may not be necessary for all procedures.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simply subsequent reference to such steps.

What is claimed is:

1. A surgical system for positioning a patient's leg during a medical procedure, the system comprising:
   a support assembly coupled to a bed and configured to support a patient's leg;
   a vertical perineal post moveably coupled to the bed, wherein the vertical perineal post is configured to move laterally relative to a longitudinal axis of the bed;
   an actuator configured to move the vertical perineal post laterally between a first position and a second position; and
   a rail coupled to the bed, wherein the rail has a longitudinal axis extending laterally relative to the longitudinal axis of the bed in top view;

wherein the vertical perineal post is movably mounted to the rail and is configured to be positioned between a patient's legs;

wherein the vertical perineal post is configured to move along the rail between the first position and the second position.

2. The system of claim 1, further comprising a bolster coupled to the bed adjacent the support assembly.

3. The system of claim 1, further comprising a control for operating the actuator.

4. The system of claim 1, wherein the longitudinal axis of the rail is oriented perpendicular to the longitudinal axis of the bed in top view.

5. The system of claim 4, wherein the vertical perineal post has a central axis oriented orthogonal to the longitudinal axis of the bed and the longitudinal axis of the rail.

6. The system of claim 5, wherein the vertical perineal post comprises an arm extending away from the bed having a cushion to interface with a patient's leg and the arm pivotable about the central axis of the vertical perineal post.

7. The system of claim 5, wherein the central axis of the vertical perineal post is repositionable with respect to the longitudinal axis of the bed and the longitudinal axis of the rail.

8. The system of claim 5, wherein the vertical perineal post comprises at least one expandable chamber configured for differential expansion.

9. The system of claim 4, wherein the rail is positioned axially adjacent to the bed and the longitudinal axis of the rail is perpendicular relative to the longitudinal axis of the bed.

10. The system of claim 9, wherein the support assembly comprises a left assembly and a right assembly configured to support the patient's corresponding left leg and right leg, and coupled to the bed at a left side and a right side.

11. The system of claim 10, wherein the rail extends between and reversibly couples to the left assembly and the right assembly.

12. An operating table system comprising,
a support assembly configured to retain each of a patient's legs and reversibly coupled to a bed;
a bolster coupled to the bed adjacent to a support assembly, wherein the bolster comprises an inner chamber configured to inflate to a first expanded position and a second expanded position;
a rail coupled to the bed, the rail having a longitudinal axis, a first end, and a second end opposite the first end, wherein the rail has a longitudinal axis extending laterally relative to a longitudinal axis of the bed in top view;
a vertical perineal post movably mounted to the rail, wherein the vertical perineal post is configured to move laterally relative to a longitudinal axis of the bed; and
an actuator configured to move the vertical perineal post laterally between a first position and a second position:
wherein the vertical perineal post is configured to move axially along the rail between the first position and the second position;
wherein the vertical perineal post is movably mounted to the rail and is configured to be positioned between a patient's legs.

13. The system of claim 12, wherein:
the longitudinal axis of the rail is oriented perpendicular to the longitudinal axis of the bed in top view;
the vertical perineal post has a central axis oriented orthogonal to the longitudinal axis of the bed and the longitudinal axis of the rail.

14. The system of claim 13, wherein the bolster is laterally repositionable between the first position and the second position with respect to a distance from the longitudinal axis of the bed.

15. The system of claim 14, wherein the bolster is configured to reversibly expand perpendicularly with respect to the longitudinal axis of the bed.

16. A method for applying traction to a patient, comprising:
securing a patient's feet to a support member to support the patient's legs distal from a bed;
positioning a perineal post between the patient's legs;
moving the perineal post laterally relative a longitudinal axis of the bed;
laterally repositioning the perineal post to apply lateral traction to the patient's leg; and
controlling an actuator to move the perineal post laterally relative to the longitudinal axis of the bed along a rail coupled to the bed, wherein the rail has a longitudinal axis extending laterally relative to the longitudinal axis of the bed in top view.

17. The method of claim 16, wherein laterally repositioning the perineal post further comprises inflating at least one expandable chamber.

18. The method of claim 16, further comprising:
positioning at least one bolster adjacent the patient's side; and
laterally repositioning the bolster;
wherein repositioning the bolster generally comprises moving the bolster in the opposite direction of repositioning the perineal post.

* * * * *